United States Patent [19]

Samain et al.

[11] Patent Number: 5,577,519
[45] Date of Patent: Nov. 26, 1996

[54] PROCESS FOR THE BLEACHING OF KERATINOUS FIBRES USING WATER VAPOUR

[75] Inventors: Henri Samain, Bievres; Jean-Michel Sturla, Saint-Cloud, both of France

[73] Assignee: L'Oreal, Paris, France

[21] Appl. No.: 356,956

[22] Filed: Dec. 16, 1994

[30] Foreign Application Priority Data

Dec. 22, 1993 [FR] France .................................. 93 15484

[51] Int. Cl.$^6$ ...................................................... A61K 7/13
[52] U.S. Cl. .................................................................. 132/208
[58] Field of Search ..................................... 132/202, 203, 132/204, 205, 206, 207, 208, 209, 210, 211

[56] References Cited

U.S. PATENT DOCUMENTS

| | | |
|---|---|---|
| 3,004,540 | 11/1961 | Ronzi . |
| 3,086,534 | 4/1963 | De Gorter et al. . |
| 4,166,473 | 9/1979 | Bauer et al. . |
| 4,341,229 | 7/1982 | Bauer et al. . |

FOREIGN PATENT DOCUMENTS

| | | |
|---|---|---|
| 103547 | 3/1984 | European Pat. Off. . |
| 1011151 | 6/1952 | France . |
| 2273492 | 1/1976 | France . |
| 1025590 | 6/1958 | Germany . |
| 357161 | 9/1961 | Switzerland . |

*Primary Examiner*—Todd E. Manahan
*Attorney, Agent, or Firm*—Finnegan, Henderson, Farabow, Garrett & Dunner, L.L.P.

[57] ABSTRACT

A process for the bleaching of keratinous fibres, in particular human keratinous fibres, characterized in that it comprises contacting the fibres with a bleaching composition containing at least one oxidizing agent and with a gas containing water vapour, the temperature of the gas being at least 75° C. and the contact time between the gas and the fibres to be bleached not exceeding ten minutes. The rapid bleaching is obtained without generating substantial reddish-brown glints.

20 Claims, No Drawings

PROCESS FOR THE BLEACHING OF KERATINOUS FIBRES USING WATER VAPOUR

The present invention is directed to a process for bleaching keratinous fibres using water vapour and a composition comprising at least one oxidizing agent.

It is well known to bleach keratinous fibres, in particular human keratinous fibres such as hair, with compositions containing an oxidizing agent. Within a few minutes, and especially in time periods of over an hour, the colour of the hair tends towards blond. It is generally observed, however, that hair thus treated also exhibits a reddish-brown glint. This reddish-brown glint is often regarded as unattractive. Thus, a rapid means of bleaching natural or dyed hair which would overcome this disadvantage has been strived for.

It has been surprisingly discovered that the use of a gas comprising water vapour, heated to a temperature of at least 75° C., preferably greater than 75° C., on hair treated with a composition comprising at least one oxidizing agent, makes it possible to obtain rapid bleaching without the generation of substantial reddish-brown glints. Moreover, following bleaching, the hair exhibits excellent final cosmetic qualities.

The use of water vapour in oxidative colouring or bleaching processes has been described in French Patent No. 1,011,151, the disclosure of which is incorporated by reference. This French patent teaches the use of water vapour, heated to approximately 50° C. to accelerate the colouring or bleaching process of the hair. However, at this temperature, this process does not obtain a decrease in the reddish-brown glints described above.

The present invention is thus directed to a process for the bleaching of keratinous fibres, comprising the step of bleaching the fibres, the fibres having previously been contacted with a bleaching composition containing at least one oxidizing agent, by contacting the fibres with a gas containing water vapour, the temperature of the gas being greater than 75° C., for a contact time between the gas and the fibres to be dyed less than ten minutes.

The present invention is also directed to a process for the bleaching of keratinous fibres, in particular human keratinous fibres, comprising the step of bleaching the fibres by contacting the fibres with a bleaching composition containing at least one oxidizing agent and with a gas containing water vapour, the temperature of the gas and the contact time between the gas and the fibres being sufficient to bleach the fibres without generating substantial reddish-brown glints.

The present invention also contemplates a process for the bleaching of keratinous fibres, in particular human keratinous fibres, comprising the step of bleaching the fibres by contacting the fibres with a bleaching composition containing at least one oxidizing agent and with a gas containing water vapour, for a time not exceeding ten minutes, preferably being less than ten minutes, and wherein the gas has a temperature sufficient to bleach the fibres without generating substantial reddish-brown glints.

A further embodiment of the present invention includes a process for the bleaching of keratinous fibres, in particular human keratinous fibres, comprising the step of bleaching the fibres by contacting the fibres with a bleaching composition containing at least one oxidizing agent and with a gas containing water vapour, the temperature of the gas being at least 75° C., preferably being greater than 75° C., and the contact time between the gas and the fibres being sufficient to bleach the fibres without generating substantial reddish-brown glints.

A still further embodiment of the present invention is thus directed to a process for the bleaching of keratinous fibres, in particular human keratinous fibres, comprising the step of bleaching the fibres by contacting the fibres with a bleaching composition containing at least one oxidizing agent and with a gas containing water vapour, the temperature of the gas being at least 75° C., preferably greater than 75° C., and the contact time between the gas and the fibres to be bleached not exceeding ten minutes, preferably being less than ten minutes.

The process of the present invention is used for the bleaching of keratinous fibres in general. The preferred form of keratinous fibres taught by the present invention is human keratinous fibres, such as hair.

The water vapour may be transported by a carrier gas that may additionally contain solvent vapour. As the vapour, gases such as oxygen or nitrogen, mixtures of gases such as air or other vapourizable compounds can also be used.

The solvents which may be used for the production of vapour are cosmetically acceptable organic solvents such as alcohols, glycols and glycol ethers. Suitable alcohols include ethanol, isopropanol, benzyl alcohol and phenylethyl alcohol. Typical glycols or glycol ethers include the monomethyl, monoethyl and monobutyl ethers of ethylene glycol, propylene glycol, butylene glycol, dipropylene glycol, and the alkyl ethers such as the monobutyl ether of diethylene glycol.

The gas preferably comprises at least 1% by volume of water vapour with respect to the total volume of the gas. The gas preferably contains either exclusively or essentially water vapour or mixtures of water vapour and air. The temperature of the gas is at least 75° C., preferably greater than 75° C. The temperature of the gas is more preferably at least 85° C. and still more preferably ranges from 85° C. to 150° C. The temperature of the gas most preferably ranges from 75° C. to less than 100° C. or from 90° C. to less than 100° C.

During the process of the present invention, the gas is contacted with the fibres for a period of time preferably ranging from 0.01 second to 5 minutes and more preferably for a period of time ranging from 10 seconds to 3 minutes. Application of the gas to the same fibres may be repeated several times, with each application being conducted for a period of time as prescribed above.

In a preferred embodiment of the present inventive process, a hair-bleaching composition containing an oxidizing agent is applied to the hair, and the hair is subsequently subjected to the action of the water vapour. Another embodiment of the present invention contemplates applying simultaneously the bleaching composition and the gas comprising water vapour to the hair. It is also possible to apply all or part of the bleaching composition to the hair using the gas flow when some or all the constituents of the composition can be entrained or vapourized. In another preferred embodiment of the invention, the application of the water vapour is followed by a rinsing with water.

The production of a hot gas comprising water vapour may be achieved using any apparatus known per se. According to the present invention, it is preferable to use an apparatus such as that described in French Patent No. 2,273,492, U.S. Pat. No. 4,166,473 or U.S. Pat. No. 4,341,229, the disclosures of which, including the drawings, are incorporated by reference, or any other equivalent apparatus, which is particularly well-suited.

The oxidizing agent is preferably chosen from hydrogen peroxide, urea hydrogen peroxide, alkali metal bromates, persalts such as perborates and persulphates and organic peroxyacids such as magnesium monoperoxyphthalate. Hydrogen peroxide is particularly preferred. The oxidizing agent may be present in concentrations ranging from 0.01% to 10% by weight with respect to the total weight of the composition.

The bleaching composition can have a pH ranging from 3 to 1.5. The pH of the bleaching composition can be adjusted to the chosen value by means of basifying agents commonly used in bleaching keratinous fibres, such as aqueous ammonia, alkali metal carbonates, alkanolamines, for example mono-, di- and triethanolamines and their derivatives, or sodium or potassium hydroxides, or of conventional acidifying agents, such as inorganic or organic acids such as, for example, hydrochloric, tartaric, citric, and phosphoric acids.

The bleaching compositions may also contain, in a preferred embodiment, anionic, cationic, non-ionic or amphoteric surface-active agents which are well-known in the art, or mixtures thereof, in proportions ranging from approximately 0.5% to 55% by weight, and preferably from 2% to 50% by weight, with respect to the total weight of the composition.

The bleaching composition may also contain organic solvents for solubilizing the components which would be insufficiently water-soluble. Preferred organic solvents include lower $C_1$–$C_4$ alkanols such as ethanol and isopropanol, glycerol and glycols; glycol ethers such as 2-butoxyethanol, propylene glycol, or the monoethyl ether and monomethyl ether of diethylene glycol; aromatic alcohols such as benzyl alcohol or phenoxyethanol; and analogous products and mixtures thereof. These solvents are preferably present in proportions ranging from approximately 1% to 40% by weight, and more preferably ranging from 5% to 30% by weight, with respect to the total weight of the composition.

It is also possible to add thickening agents chosen, for example, from optionally cross-linked acrylic acid polymers or inorganic thickening agents such as bentonite which are preferably present in proportions ranging from approximately 0.1% to 5%, and more preferably from 0.2% to 3%, by weight with respect to the total weight of the composition.

Antioxidizing agents can also be introduced to the bleaching compositions. They are preferably chosen from sodium sulphite, thioglycolic acid, thiolactic acid, sodium bisulphite, dehydroascorbic acid, hydroquinone, 2-methylhydroquinone, 2-(tert-butyl)hydroquinone and homogentisic acid. They are present in proportions ranging from approximately 0.05% to 1.5% by weight with respect to the total weight of the composition.

The bleaching compositions can also contain other cosmetically acceptable adjuvants such as penetrating agents, sequestrating agents, fragrances, buffers, dispersing agents, treating agents, conditioning agents, film-forming agents, preserving agents and opacifying agents.

The bleaching compositions used in the process of the present invention can be provided in forms commonly used for bleaching hair such as a more or less thickened or gelled liquid, a cream, an aerosol foam or in any other form appropriate for carrying out the bleaching of hair.

The examples which follow illustrate the invention without limiting the scope of the invention.

EXAMPLE 1

The same lightening mixture was applied to two locks of dark brown hair, this mixture had the following composition (this mixture was obtained by mixing Composition A with Composition B and then mixing with hydrogen peroxide):

| | |
|---|---|
| Composition A | 60 g |
| Composition B | 50 g |
| 30 Volumes hydrogen peroxide (pH 3) | 120 ml | with:

| | |
|---|---|
| Composition A: | |
| Nonylphenol oxyethylenated with 4 mol of ethylene oxide | 25 g |
| Nonylphenol oxyethylenated with 9 mol of ethylene oxide | 20 g |
| Lauric acid oxyethylenated with 2 mol of ethylene oxide | 7 g |
| Oleic acid | 30 g |
| Propylene glycol | 12 g |
| Aqueous ammonia (20% of $NH_3$) | 7 g |
| Demineralized water | 100 g |
| Composition B: | |
| Sodium persulphate | 30 g |
| Potassium persulphate | 25 g |
| Anhydrous sodium disilicate | 3 g |
| Colloidal silica | 0.4 g |
| Ammonium chloride | 12 g |

One lock (Lock No. 1) was subjected to a conventional treatment: 30 min at room temperature. The other lock (Lock No. 2) was subjected to a treatment with water vapour according to the invention, namely a treatment for 1 min 30 sec with water vapour at 90° C. The bleaching results, which were assessed in this instance by measuring the chromaticity coordinates of each of the two locks in the L, a, b system (Minolta Chroma Meter CR 200 colorimeter), were as follows:

| | L | a | b |
|---|---|---|---|
| Lock No. 1 | 34.15 | 11 | 19.7 |
| Lock No. 2 | 34.1 | 9.4 | 18.5 |

The locks had been lightened to an equivalent degree (L near enough the same) but the shades were less reddish-brown in the case of hair treated with water vapour (the values a and b were lower and consequently the shade was less red and less yellow).

EXAMPLE 2

The same lightening mixture as that of Example 1 was applied to two locks of dark brown hair. One lock (Lock No. 1) was subjected to two treatments: two times one hour at room temperature. The other lock (Lock No. 2) was subjected to a treatment with water vapour according to the invention, namely two treatments each for 2 min with water vapour at 90° C. The bleaching results (Minolta Chroma Meter CR 200 colorimeter) were as follows:

| | L | a | b |
|---|---|---|---|
| Lock No. 1 | 59.7 | 7.3 | 31.9 |
| Lock No. 2 | 59.8 | 5.8 | 27 |

As in Example 1, the locks had been lightened to an equivalent degree (L near enough the same) but the shades were less reddish-brown in the case of hair treated with water vapour (Lock No. 2).

What is claimed is:

1. A process for the bleaching of keratinous fibres, comprising the step of:

bleaching said fibres, said fibres having previously been contacted with a bleaching composition containing at least one oxidizing agent, by contacting said fibres with a gas containing water vapour, the temperature of the gas being greater than 75° C., for a contact time between said gas and said fibres to be dyed less than ten minutes.

2. A process according to claim 1, wherein the gas has a temperature of at least 85° C.

3. A process according to claim 2, wherein the gas has a temperature ranging from 85° C. to 150° C.

4. A process according to claim 1, wherein the gas is contacted with the fibres to be bleached for a period of time ranging from 0.01 second to 5 minutes.

5. A process according to claim 4, wherein the gas is contacted with the fibres to be bleached for a period of time ranging from 10 seconds to 3 minutes.

6. A process according to claim 1, wherein the application of the gas on the fibres is repeated several times.

7. A process according to claim 1, wherein the gas contains exclusively water vapour.

8. A process according to claim 1, wherein the gas contains water vapour and at least one other compound in the form of gas or vapour.

9. A process according to claim 8, wherein the gas contains water vapour and air.

10. A process according to claim 1, wherein said at least one oxidizing agent is selected from hydrogen peroxide, urea hydrogen peroxide, alkali metal bromates, persalts such as perborates and persulphates, and organic peroxyacids such as magnesium monoperoxyphthalate.

11. A process according to claim 1, wherein said at least one oxidizing agent is present in concentrations ranging from 0.01% to 10% by weight with respect to the total weight of the composition.

12. A process according to claim 1, wherein said keratinous fibres are human keratinous fibres.

13. A process according to claim 1, wherein the temperature of the gas ranges from 75° C. to less than 100° C.

14. A process according to claim 1, wherein the temperature of the gas ranges from 90° C. to less than 100° C.

15. A process for the bleaching of keratinous fibres, comprising the step of:

bleaching said fibres by contacting said fibres with a bleaching composition containing at least one oxidizing agent and with a gas containing water vapour, the temperature of said gas being at least 75° C. and the contact time between said gas and said fibres being sufficient to bleach said fibres without generating substantial reddish-brown glints.

16. A process according to claim 15, wherein said keratinous fibres are human keratinous fibres.

17. A process for the bleaching of keratinous fibres, comprising the step of:

bleaching said fibres by contacting said fibres with a bleaching composition containing at least one oxidizing agent and with a gas containing water vapour, the temperature of said gas being at least 75° C. and the contact time between said gas and said fibres to be bleached not exceeding ten minutes.

18. A process according to claim 17, wherein said fibres are contacted with the gas containing water vapour simultaneously with said fibres being contacted with a bleaching composition containing at least one oxidizing agent.

19. A process according to claim 17, wherein said fibres are contacted with the gas containing water vapour subsequent to said fibres being contacted with a bleaching composition containing at least one oxidizing agent.

20. A process according to claim 17, wherein said keratinous fibres are human keratinous fibres.

* * * * *